United States Patent [19]
Townsend

[11] Patent Number: 5,693,007
[45] Date of Patent: Dec. 2, 1997

[54] PRE-ASSEMBLED CUSTOM FIT KNEE ORTHOSIS AND METHOD OF MAKING SAME

[75] Inventor: Jeffrey Townsend, Bakersfield, Calif.

[73] Assignee: Townsend Design, Bakersfield, Calif.

[21] Appl. No.: 604,304

[22] Filed: Feb. 21, 1996

[51] Int. Cl.⁶ .................................................. A61F 5/00
[52] U.S. Cl. ........................... 602/26; 602/6; 602/7; 602/8; 602/16
[58] Field of Search ...................... 602/5–8, 16, 18, 602/20, 23, 26; 264/222, 223, DIG. 30

[56] References Cited

U.S. PATENT DOCUMENTS

| | | | |
|---|---|---|---|
| 4,387,709 | 6/1983 | Shen | 602/26 |
| 4,672,955 | 6/1987 | Cooper | 602/16 X |
| 5,215,517 | 6/1993 | Stevenson et al. | 602/18 |
| 5,288,287 | 2/1994 | Castillo et al. | 602/26 X |
| 5,372,572 | 12/1994 | Tamagni | 602/26 X |
| 5,382,223 | 1/1995 | Springs | 602/26 X |
| 5,415,625 | 5/1995 | Cassford et al. | 602/26 |
| 5,458,565 | 10/1995 | Tillinghaust, III et al. | 602/26 |
| 5,554,104 | 9/1996 | Grim | 602/26 X |

*Primary Examiner*—Linda C. Dvorak
*Attorney, Agent, or Firm*—Sixbey, Friedman, Leedom & Ferguson; David S. Safran

[57] ABSTRACT

A method and apparatus for forming a custom fit knee orthosis is disclosed that includes forming a flat pre-assembled knee orthosis in which upper and lower support blanks made of rigid carbon fiber and plastic resin composite materials are connected in a flat, rigid state by joint mechanisms, and the knee orthosis is shipped to a orthopedist or orthopedic assembly facility in a flat condition with the blanks of composite material still in their flat pre-cured state. The orthopedist or orthopedic assembly facility heat softens the blanks and reshapes them to conform to the contours of a particular patient's leg, with only minor finishing operations being required after the reshaped blanks have set.

14 Claims, 5 Drawing Sheets

PRE-ASSEMBLED CUSTOM FIT KNEE ORTHOSIS AND METHOD OF MAKING SAME

BACKGROUND OF THE INVENTION

1. Field of the Invention

This invention relates to orthopedic devices for individuals whose knee has been weakened by injury, and for whom support and stabilization of the knee is necessary. In particular, the present invention relates to a method and apparatus for producing a custom fit orthopedic device.

2. Description of Related Art

Orthopedic devices, specifically knee orthoses, are available in two major types, off-the-shelf and custom fit. Off-the-shelf knee orthoses are completely pre-made by a manufacturer and do not have thigh and calf support portions that are formed to fit a particular user's leg, while custom fit knee orthoses do have shell-type support members molded to conform to the shape of a specific user's leg. Off-the-shelf knee orthoses are generally shipped from a manufacturer in their completed state, where the thigh and calf support portions are curved to generally conform to the arcuate nature of a user's leg. Shipping of such orthoses requires the use of large, bulky containers due to the pre-shaping of leg support portions of the orthoses. Custom fit knee orthoses, on the other hand, are sent in parts to a physician or an orthopedic assembling facility, or the like, that will complete the assembly of the knee orthosis either directly on the patient's leg or according to a mold of the patient's leg. Such parts include a thigh support portion, a calf support portion, hinges, struts, suspension straps, etc. Typically, none of the parts are pre-assembled to one another when shipped. For example, the thigh support portion is not pre-connected to the calf support portion. FIG. 7 shows one reason why this is done.

FIG. 7 depicts aluminum blanks for forming a known off-the-shelf type knee brace, prior to bending to a leg contour. From this figure, it can be seen that, in the unshaped, flat condition shown, a medial-lateral distance B of a thigh support portion 10 is greater than a medial-lateral distance A of the calf support portion 20, and therefore, the two portions cannot be connected by a joint mechanism until they have been shaped to conform at least generally to the contour of a human leg. On the other hand, with a custom fit knee orthosis, the parts can be sent in a flat state, because it is not assembled until received by the physician or assembling shop who will perform the necessary contouring of the support portions; therefore, shipping costs are generally less for a custom fit orthosis than for the off-the-shelf type knee orthosis; although, the fitting process is more costly.

A typical knee orthosis is shown in U.S. Pat. No. 5,042,464 to Skwor et al. The knee orthosis includes rigid thigh and calf cuffs or cross members, and includes upper and lower medial and lateral bars or struts that are connected by hinges, thereby permitting pivotal movement of the knee. In addition, attachment straps are used to secure the orthosis to the leg of the user together with cross members running between the lateral and medial struts. Skwor et al. further discloses the use of a pad disposed on an interior surface of the cross members, the pads being pliable when placed on a user's leg, so that they deform to conform to the shape of the user's leg, and after which they harden. This type of pad, apparently, enables the orthosis to be sized, molded, fit, and dispensed in a few hours, such that the orthosis provides a degree of custom fitting to an off-the-shelf type orthosis. The Skwor et al. design, however, like more conventional off-the-shelf type knee orthoses, must be transported from the manufacturer to a physician or assembling shop in its finished shape (except for the possible molding of the above-mentioned pads), the cross members having been preformed to their usable contoured shape to generally fit a user's leg. Therefore, just as with other off-the-shelf orthoses, the Skwor et al. orthosis requires large, bulky containers for shipping, unnecessarily increasing shipping costs. In addition, the Skwor et al. orthosis suffers from the problem that the cross members of the orthosis having been contoured by the manufacturer to a standard leg size, and may not be correctly shaped for a particular patient's leg, so that even the conforming nature of the pad may not be enough to compensate for incorrect sizing and/or contouring which may exist. Therefore, the Skwor et al. orthosis still suffers from major disadvantages associated with standard off-the-shelf type knee orthoses.

U.S. Pat. No. 4,672,955 to Cooper provides an example of a custom fit knee orthosis. In the Cooper design, four subassemblies, each including a support portion and a sidebar or strut are transported to a physician or other such specialist who then connects the upper and lower support portions to form the orthosis while the subassemblies are worn by a user. The subassemblies are made from suitable pre-impregnated composite materials, such as glass fiber impregnated with polyester resin, which have been partially cured. The Cooper orthosis, however, also suffers from the above-mentioned problem that the subassemblies are partially cured in their bent shape and therefore require large, bulky containers for shipping. In addition, the physician must still connect the thigh support portions to the calf support portions, including assembling the hinge portion using a complicated joint fixture, all of which is done while the patient is wearing the whole assembly. This process of connecting the subassemblies may make the user uncomfortable for some considerable period of time considering that the user's leg is already weakened by injury.

Other conventional designs for knee orthoses are disclosed in U.S. Pat. Nos. 5,372,572 to Tamagni and 5,382,223 to Springs. The above-discussed problems with the prior art indicate that the need exists for a custom molded knee orthosis which reduces the assembly time and effort by a physician or assembling shop so as to be close to an off-the-shelf orthosis without increasing the costs of shipping the orthosis from the manufacturer to the physician or assembling shop to that associated with off-the-shelf orthoses.

SUMMARY OF THE INVENTION

It is a primary object of the present invention to overcome the disadvantages of the prior art and to provide a method and apparatus for forming a custom fit knee orthosis that permits an almost fully assembled custom fit knee orthosis to be shipped in a flat state to a physician or orthopedic assembling facility.

It is another object of the present invention to provide a method and apparatus for forming a custom fit knee orthosis that greatly reduces the shipping costs associated with a typical off-the-shelf type knee orthosis, and also reduces a physician's work in assembling and fitting the knee orthosis.

These and other objects that will become apparent in the following description are achieved in accordance with a preferred embodiment of the invention. In particular, a method and apparatus for forming a knee orthosis is provided that includes forming a pre-assembled knee orthosis of upper and lower support blanks which are made of pre-cured, rigid fiber and resin composite materials, femoral and tibial struts of the blanks being connected by joint mechanisms in a manner enabling the pre-assembled knee orthosis to be shipped in a flat state, and then the composite material of the shipped, pre-assembled knee orthosis being heated to allow it to be re-shaped to conform with the contours of a patient's leg by the doctor or assembly facility.

These and further objects, features and advantages of the present invention will become apparent from the following description when taken in connection with the accompanying drawings which, for purposes of illustration only, show a preferred embodiment in accordance with the present invention.

DETAILED DESCRIPTION OF THE PREFERRED EMBODIMENT

Figure 1:
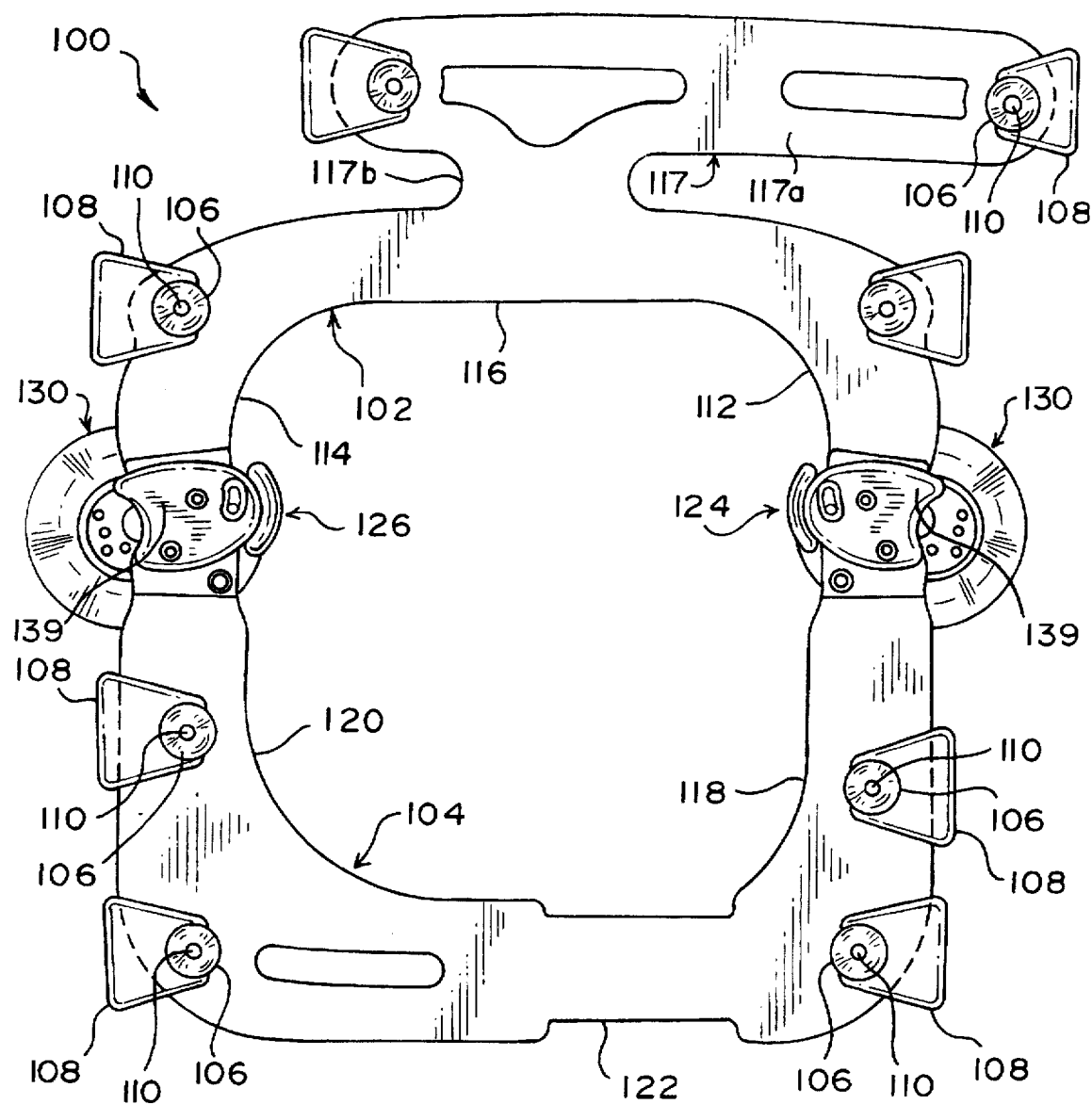
FIG. 1 is a schematic plan view of a preassembled custom fit knee orthosis in accordance with the present invention.
Figure 3:
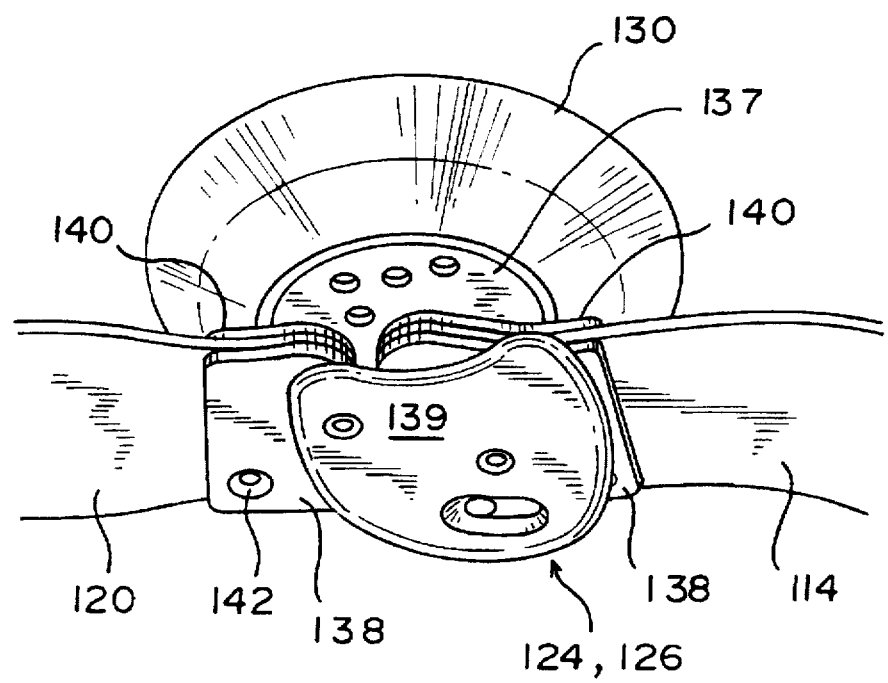
FIG. 3 is a distal perspective view of the joint mechanism of the custom knee orthosis in accordance with the present invention.
Figure 2:
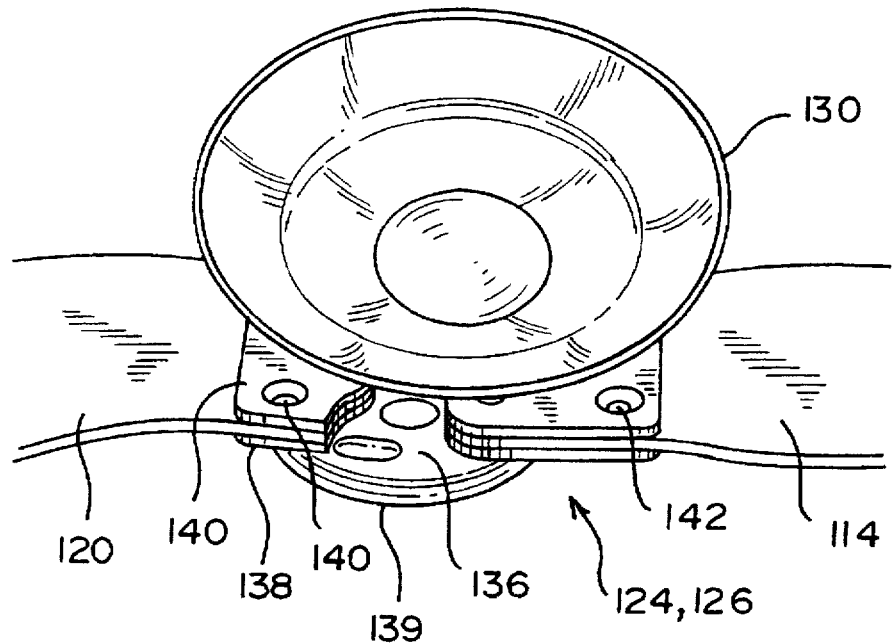
FIG. 2 is a proximal perspective view of a joint mechanism of the custom knee orthosis in accordance with the present invention.
Figure 5:
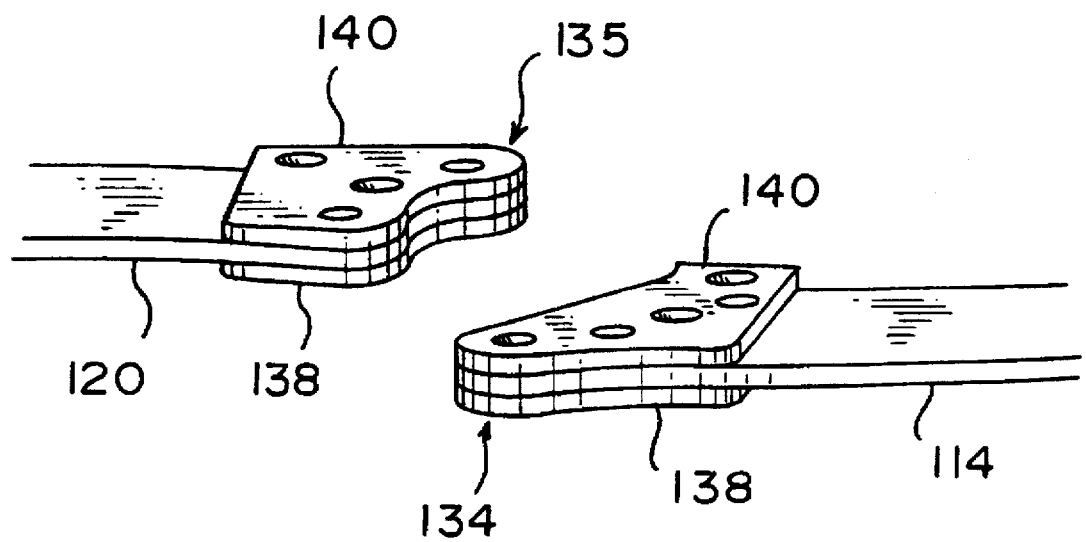
FIG. 5 is a perspective view of reinforced strut ends of the custom knee orthosis blanks in accordance with the present invention.
Figure 4:
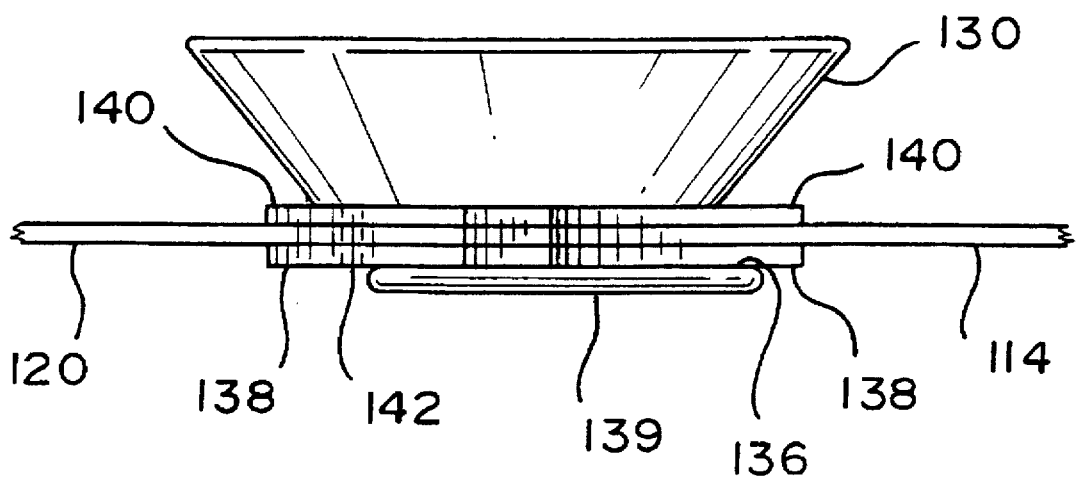
FIG. 4 is a schematic side view of the joint mechanism of the present invention.

FIG. 1 is a schematic plan view of a pre-assembled custom fitting knee orthosis 100 in accordance with the present invention in a flat state, i.e., prior to shaping of it to fit a particular patient. Knee orthosis 100 includes a rigid, upper support blank 102 for forming a thigh support portion of a finished orthosis and a rigid lower support blank 104 for forming a calf support portion of a finished orthosis. The thigh support blank 102 includes a lateral femoral strut forming portion 112, a medial femoral strut forming portion 114, and one or more shell-type upper cross member portions 116 that will pass around the front of a patient's leg when the blank 102 is re-shaped, as is described below, as well as an outrigger thigh support band forming portion 117 of an asymmetric T-shape which has a femor valgus angle accommodating portion 117a connected to the cross member forming portion 116 by a connecting neck portion 117b. The calf support blank 104 includes a lateral tibial strut forming portion 118, a medial tibial strut forming portion 120, and a shell-type lower cross member forming portion 122 that will conform to the shape of the patient's leg once the blank 104 is re-shaped and set.

In addition, heat-resistant chafes 106 hold heat-resistant loops 108 in place using black oxide steel, or other hard metal, rivets 110. Loops 108 are used for connecting suspension straps via a Velcro®, hook and loop type fabric attachment means (not shown). It is noted that the chafes 106, loops 108, and rivets 110 shown are only one approach to connecting suspension straps, and any other conventional connecting means may be alternatively used.

The upper and lower blank 102, 104 of the knee orthosis 100 are connected by a lateral joint mechanism 124 and a medial joint mechanism 126. While some of the details of joint mechanisms 124, 126 are not depicted, any typical joint mechanism that permits pivotal movement of the struts relative to each other may be utilized. However, a preferred joint mechanism is that which forms the subject of one of the present applicant's U.S. Pat. No. 5,259,832, the contents of which are incorporated herein by reference to the extent necessary to complete an understanding of the present invention. Shown connected to the joint mechanisms 124, 126 are rubber condyle pads 130 which have a spherical cup-shape on a side that will face the patient's knee once the orthosis has been completed. While the rubber condyle pads 130 are shown attached to the knee orthosis 100 in the FIG. 1 flat shipping state, in practice they will be packaged with orthosis 100 detached therefrom, and are attached to the inner pivot plates 139, as described below, after the custom re-shaping of the knee orthosis to fit a particular patient. Such pads may include a recessed gel insert to increase comfort for the user, and may have a recess within which pivot plate 139 is received.

FIGS. 2–5 depict one of the joint mechanisms 124, 126 in further detail (both joint mechanisms are depicted as the same, here, but do not have to be), including reinforcing support plates 138, 140 which may be made of stainless steel or other rigid metal, outer pivot plate 136, inner pivot plate 137 and the condyle pad 130. The support plates 138, 140 are attached to the lower ends 134 of the femoral struts 112, 114, and to the upper ends 135 of the tibial struts 118, 120, e.g., by stainless steel, or other hard metal, rivets 142. Likewise, the strut ends 134, 135, are linked by the outer and inner pivot plates 136, 137 via such rivets.

Figure 7:
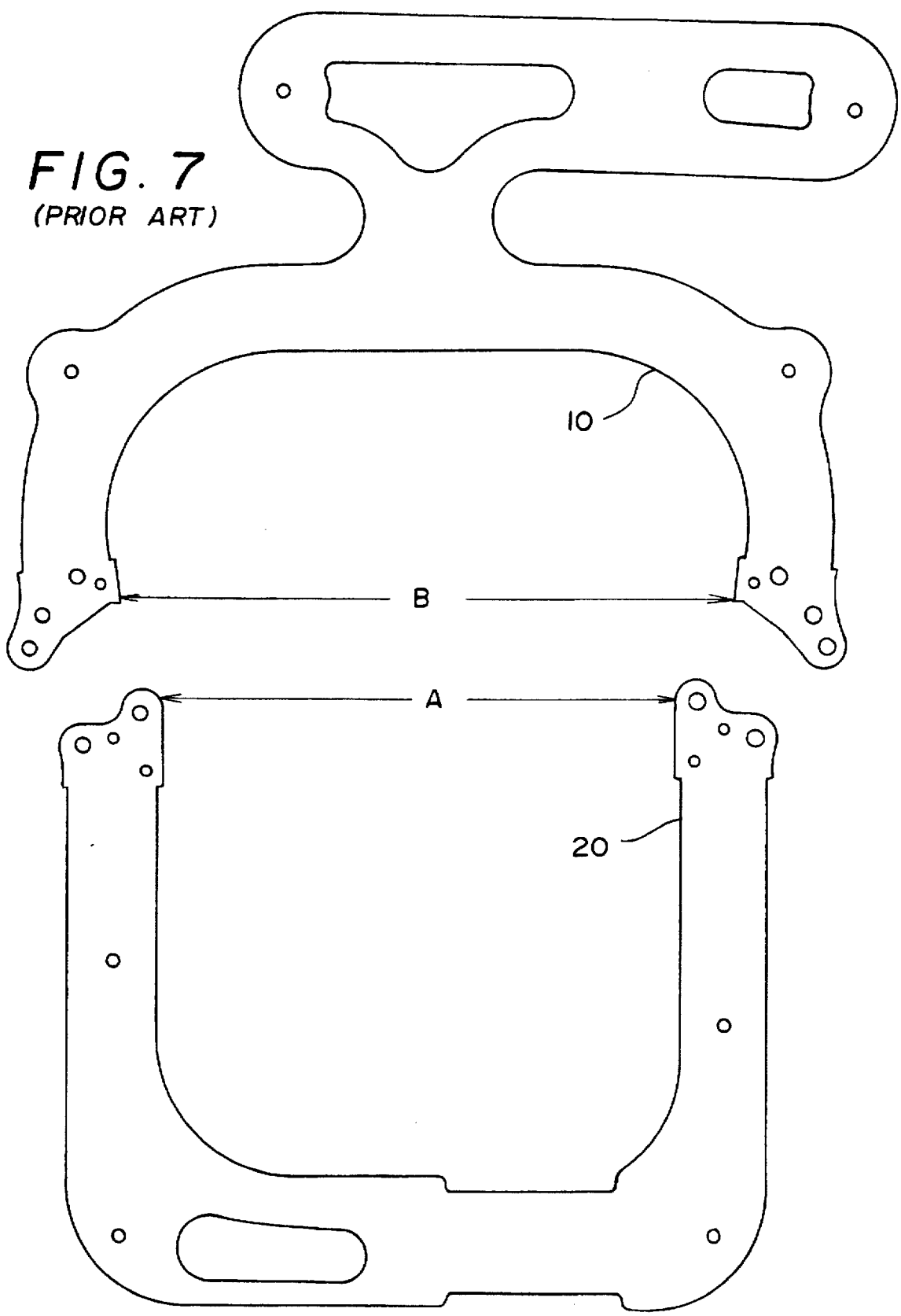
FIG. 7 is a schematic plan view of knee orthosis blanks showing typical medial-lateral distances of upper and lower support portions of a conventional off-the-shelf knee orthosis.

The pre-assembled, custom fit knee orthosis 100 provides many advantages over the prior art. For one, previous custom fit knee orthoses were formed from an upper support portion blank that is not attached to the lower support portion blank via joint mechanisms when the parts are shipped to the physician or orthopedic assembling facility, while the present invention permits the manufacturer to form an almost completely finished orthosis that needs essentially only to be re-shaped by the physician or assembling facility, and then, to have hinge caps, condyle pads and straps attached to be complete. In this regard, as noted above, typical knee orthosis blanks have an upper support portion that has a medial-lateral distance B that is larger than the medial-lateral distance A of the lower support portion, as shown in FIG. 7, so that they cannot be connected by a hinging mechanism until they have been shaped. With the present knee orthosis 100, the manufacturer can connect thigh support portion 102 and calf support portion 104 using joint mechanisms 124, 126 before shipping out the orthosis, and the physician or assembling facility only has to mold and set the blanks 102, 104 of the orthosis 100 in conformance with the contours of the particular patient's leg to achieve a custom fit knee orthosis.

In addition, because the knee orthosis blank 100 is manufactured and shipped to the physician or assembling facility in a flat condition, this eliminates the necessity of large, bulky containers that can increase shipping costs and are more difficult to handle. Overall, the present invention provides the convenience of an off-the-shelf knee orthosis that is sent by a manufacturer in a substantially completed state in which the joint mechanisms are attached connecting the calf and thigh support portions of the orthosis, while retaining the advantage of having a custom fit knee orthosis whose parts are shipped in a flat condition to save shipping costs and to provide ease in handling.

Figure 6:
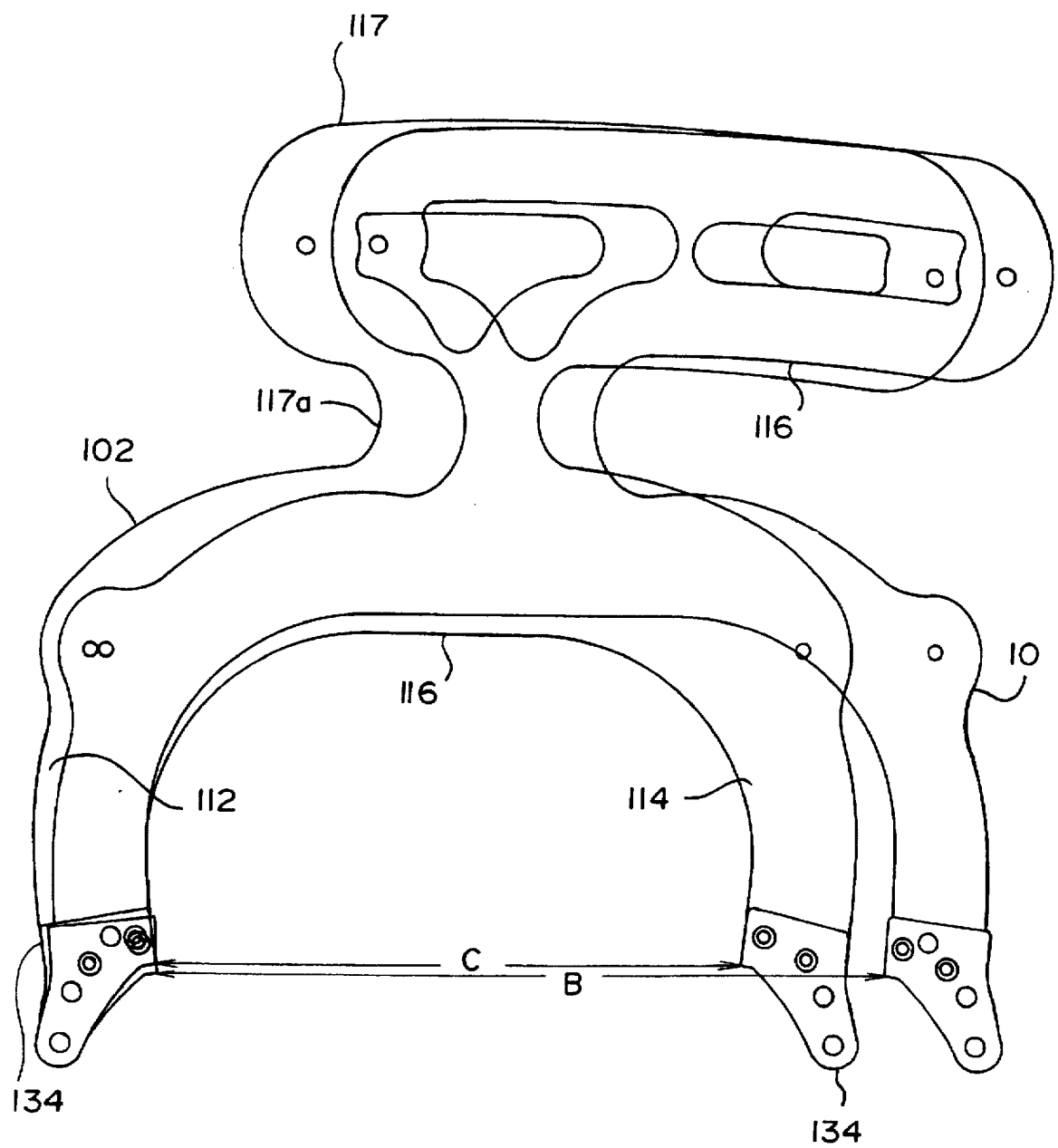
FIG. 6 are superposed plan views of the upper support portion of the off-the-shelf knee orthosis blank of FIG. 7 and the upper support portion of the custom fit knee orthosis blank in accordance with the present invention of FIG. 1.

For the manufacturer to connect the thigh support blank 102 and the calf support blank 104 via the joint mechanisms 124, 126 before the knee orthosis blank is shipped out to a physician or assembling shop, the thigh support blank 102 has to be given a medial-lateral distance C between the ends 134 of the femoral strut forming portions 112, 114 that* is essentially the same as a medial-lateral distance A of calf support blank 104 as opposed to the greater medial-lateral distance B of the corresponding thigh support portion 10 of the conventional blank shown in FIGS. 6 and 7. To do so, the proximal section (i.e., the inverted U-shaped portion composed of the femoral strut forming portions 112, 114 and the cross member forming portion 116) has been narrowed as is apparent from the superposed blanks shown in FIG. 6. However, since this reduces the radius of the proximal section when wrapped around the thigh, if merely narrowed to position the joining support plates 134 in alignment with the support plates 135 of the calf support blank 104, the lateral and medial struts 112, 114 would be shifted anteriorly, creating fit and support problems. Thus, the flexion angle of the lateral and medial femoral struts 112, 114, in accordance with the present invention, has also been changed in an anterior direction to prevent edge pressure on the proximal thigh area and to accommodate its conical shape, thereby allowing the proximal end of the thigh to move in an anterior direction. On the other hand, while the struts 112, 114, cross member 116 and neck 117a have been widened for extra support, as shown in FIG. 6, such is not essential. Furthermore, while an outrigger type support 117 is a known type of thigh securing mechanism, it takes on special significance in the context of the present invention in that other forms of thigh supports which extend higher up the thigh have been found unsuitable for use with the present invention.

While any moldable rigid composite material may be used for the knee orthosis blanks 102, 104, preferably, a graphite and acrylic composite sheet material, and more specifically TL-6000 acrylic graphite thermoplastic composite sheet material, produced by Medical Materials Corporation, has been found to be particularly suitable for manufacturing the thigh support blank 102 and the calf support blank 104 because this graphite and acrylic composite material provides for lightweight, low profile solutions that provide greater rigidity and strength relative to other materials, and is pre-cured, eliminating the need for wet lay-up. Of course, as mentioned above, any moldable rigid composite material that can be re-shaped as needed, after heat re-softening, may be utilized.

Now, one possible method for manufacturing and assembling the custom fit knee orthosis 100 of the present invention will be described in detail. While any of the steps may be performed by anyone, the first set of steps is preferably performed by the manufacturer, while the second set of steps is preferably performed by a physician or orthopedic appliance assembling facility. In the first set of steps, the composite material thigh and calf support blanks 102, 104 are stamped to specifications from rigid sheets of the composite material. Edges of the support blanks 102, 104 are beveled and polished prior to assembly. Next, support plates 138, 140 are attached to the free ends 134 of strut forming portions 112, 114, and the free ends 135 of strut forming portions 118, 120. Then, inner and outer pivot plates 136, 137 are attached to femoral and tibial strut ends 134, 135. The heat-resistant chafes 106 and loops 108 are attached at appropriate locations on thigh and calf support blanks 102, 104 using, e.g., black oxide steel rivets 110. The pre-formed knee orthosis 100 is now completed, and is packaged and sent to a physician or assembling facility in a flat condition, along with suspension straps (not shown), condyle pads 130, and compressed foam pads with a lycra backing (not shown).

The second set of steps in the process will then be performed by an orthopedic physician or assembling facility. At this point, the knee orthosis can be formed over a ¼" to ³⁄₁₆" thick neoprene sleeve interface, either directly on a patient's leg or using a positive impression of the patient's leg. The neoprene sleeve, in addition to providing thermal insulation, provides a spatial allowance for the compressed foam pads which are be added afterwards. Assuming that a positive impression model of the patient's leg is made, the pre-assembled knee orthosis 100 is heated in a convection, conduction or infrared oven at a temperature between 380°–400° F. for five to seven minutes, preferably at 400° for approximately seven minutes to sufficiently soften the blanks. Then, the knee orthosis 100 is draped over this impression model, compressed with an elastic bandage or bladder, and permitted to cool for approximately three to four minutes (or longer) to allow the re-shaped blanks to re-set. The joint mechanisms 124, 126 are then squared in an alignment fixture. The compressed foam pads are then attached to the back of the thigh and calf support portions 102, 104, the condyle pads 130 are attached to inner pivot plates 137, for example by gluing, and then suspension straps are attached to the loops 108 and cut to length. Lastly, any joint mechanism cover plates 139 are attached to complete the custom fit knee orthosis.

It should be noted that this second set of steps can be performed easily and quickly. Therefore, a user can receive a custom fitted knee orthosis in a matter of hours after taking the positive impression model. As noted previously, the manufacturer is able to almost completely assemble the knee orthosis, including attaching the joint mechanisms 124, 126, and attachment strap receiving loops 108, and can ship this pre-assembled knee orthosis 100 to the physician or assembling facility in a flat state, thereby saving both shipping costs and assembly time and expense on the part of the physician or assembling shop.

While one embodiment in accordance with the present invention has been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

I claim:

1. A method for forming a custom fit knee orthosis, comprising the steps of:

forming a thigh support blank from a sheet of a pre-cured, rigid fiber and resin composite material, said blank having a lateral femoral strut forming portion connected with a medial femoral strut forming portion by a cross member forming portion;

forming a calf support blank from a sheet of a pre-cured, rigid fiber and resin composite material, said blank having a lateral tibial strut forming portion connected with a medial tibial strut forming portion by a cross member forming portion;

forming said blanks into a pre-assembled knee orthosis by connecting said lateral femoral strut forming portion with said lateral tibial strut forming portion via a lateral joint mechanism, and by connecting said medial femoral strut forming portion with said medial tibial strut forming portion by a medial joint mechanism; and shipping said pre-assembled knee orthosis in a flat condition with the composite material still in a flat pre-cured rigid state.

2. The method of forming a knee orthosis of claim 1, further comprising the steps of heating the rigid composite material of the shipped, pre-assembled knee orthosis to soften it; reshaping the softened composite material into a shape conforming with the contours of a patient's leg; and cooling said composite material to fix the composite material in said shape.

3. The method of forming a knee orthosis of claim 2, wherein said heating step is performed at a temperature in a range of about 380°–400° F.

4. The method of forming a knee orthosis of claim 3, wherein the step of forming said blanks into a pre-assembled knee orthosis includes the steps of attaching strap-receiving loops, which are formed of a material which is resistant to the temperature of said heating step, to said blanks.

5. The method of forming a knee orthosis of claim 2, wherein said step of reshaping the softened composite material is performed over a ¼" neoprene interface.

6. The method of forming a knee orthosis of claim 5, wherein a pressure-applying bladder or elastic bandage is applied over the knee orthosis after said reshaping step for maintaining said shape during said cooling step.

7. A pre-assembled knee orthosis for custom fitting to a patient's leg, comprising:

a thigh support blank made of a sheet of a pre-cured, rigid fiber and resin composite material, said blank having a lateral femoral strut forming portion connected with a medial femoral strut forming portion by a cross member forming portion;

a calf support blank made a sheet of a pre-cured, rigid fiber and resin composite material, said blank having a lateral tibial strut forming portion connected with a medial tibial strut forming portion by a cross member forming portion;

wherein said lateral femoral strut forming portion is connected with said lateral tibial strut forming portion via a lateral joint mechanism, and said medial femoral strut forming portion is connected with said medial tibial strut forming portion by a medial joint mechanism; and wherein said pre-assembled knee orthosis is packaged for shipping in a flat condition with the composite material still in a flat pre-cured, rigid state.

8. A pre-assembled knee orthosis according to claim 7, wherein said composite material is reshapable by being softened at a temperature in the range of about 380°–400° F.

9. A pre-assembled knee orthosis according to claim 7, wherein strap-receiving loops, which are formed of a material which is resistant to the temperature at which said composite material is softenable, is connected to said blanks.

10. A pre-assembled knee orthosis according to claim 7, wherein said composite material is an acrylic graphite thermoplastic composite material.

11. A pre-assembled knee orthosis according to claim 7, wherein metal support plates are mounted over an end of each of said strut forming portions of the blanks, said joint mechanisms being attached at said support plates.

12. A pre-assembled knee orthosis according to claim 7, wherein the thigh support blank has an inverted U-shaped portion forming the femoral strut forming portions and the cross member forming portion, and also has an outrigger thigh support band forming portion with a femor valgus angle accommodating portion that is connected to the cross member forming portion by a connecting neck portion.

13. A preassembled knee orthosis according to claim 12, wherein the outrigger thigh support band has an asymmetric T-shape.

14. A pre-assembled knee orthosis according to claim 12, wherein the femoral struts have an anteriorly directed flexion angle which prevent edge pressure on a proximal thigh area of a wearer's leg and accommodate its conical shape.

* * * * *